US006290981B1

(12) United States Patent
Keefer et al.

(10) Patent No.: US 6,290,981 B1
(45) Date of Patent: Sep. 18, 2001

(54) USE OF NITRIC OXIDE-RELEASING AGENTS TO TREAT IMPOTENCY

(75) Inventors: Larry K. Keefer, Bethesda; Joseph E. Saavedra, Thurmont, both of MD (US); Paul C. Doherty, Cupertino; Mark S. Hanamoto, Belmont, both of CA (US); Virgil A. Place, Kawaihae, HI (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/289,570

(22) Filed: Apr. 9, 1999

Related U.S. Application Data

(60) Division of application No. 08/419,044, filed on Apr. 10, 1995, now Pat. No. 5,910,316, which is a continuation-in-part of application No. 08/121,169, filed on Sep. 14, 1993, now Pat. No. 5,525,357, which is a continuation-in-part of application No. 07/935,565, filed on Aug. 24, 1992, now Pat. No. 5,405,919.

(51) Int. Cl.[7] .............................. A61K 3/785; A61J 3/00
(52) U.S. Cl. .................. 424/423; 424/78.08; 514/968; 604/517
(58) Field of Search ................. 604/517; 424/78.08, 424/423

(56) References Cited

U.S. PATENT DOCUMENTS

| 3,153,094 | 10/1964 | Reilly . |
| 3,826,832 | 7/1974 | Anderson et al. . |

(List continued on next page.)

FOREIGN PATENT DOCUMENTS

| 2106105 | 3/1995 | (CA) . |
| 2126035 | 12/1971 | (DE) . |
| 211789 | 7/1984 | (DE) . |
| 425154 | 10/1990 | (EP) . |
| 0 432 199 | 7/1993 | (EP) . |
| WO 89/12627 | 6/1989 | (WO) . |
| WO 90/09785 | 9/1990 | (WO) . |
| WO 91/04022 | 4/1991 | (WO) . |
| WO 91/05551 | 5/1991 | (WO) . |
| WO 92/05149 | 4/1992 | (WO) . |
| WO 93/07114 | 4/1993 | (WO) . |
| WO 93/15779 | 8/1993 | (WO) . |
| WO 93/20088 | 10/1993 | (WO) . |
| WO 93/20806 | 10/1993 | (WO) . |
| WO 95/10267 | 4/1995 | (WO) . |
| WO 95/24898 | 9/1995 | (WO) . |

OTHER PUBLICATIONS

Adams et al., *Radiation Research*, 67, 9–20 (1976).
Alston et al., *J. Biol. Chem.*, 260 (7), 4069–4074 (1985).
Ames et al., *Proc. Natl. Acad. Sci. USA*, 78, 6858–6862 (1981).
Andrade et al., *Br. J. Pharmacol.*, 107, 1092–1095 (1992).

(List continued on next page.)

*Primary Examiner*—Peter F. Kulkosky
(74) *Attorney, Agent, or Firm*—Leydig, Voit & Mayer, Ltd.

(57) ABSTRACT

A method of treatment for impotency is provided. The method involves the administration of nitric oxide by a nitric oxide-releasing agent capable of providing a penile erection-inducing amount of nitric oxide to the corpus cavernosum of the penis of an impotent male animal. Also provided is a nitric oxide delivery means for use in the method.

10 Claims, 3 Drawing Sheets

U.S. PATENT DOCUMENTS

| | | |
|---|---|---|
| 4,127,118 | 11/1978 | Latorre . |
| 4,265,714 | 5/1981 | Nolan et al. . |
| 4,482,533 | 11/1984 | Keith . |
| 4,638,079 | 1/1987 | Inskip et al. . |
| 4,708,854 | 11/1987 | Grinstead . |
| 4,801,587 | 1/1989 | Voss et al. . |
| 4,829,991 | 5/1989 | Boeck . |
| 4,921,683 | 5/1990 | Bedell . |
| 4,952,289 | 8/1990 | Ciccone et al. . |
| 4,954,526 | 9/1990 | Keefer . |
| 4,985,471 | 1/1991 | Ohta et al. . |
| 5,039,705 | 8/1991 | Keefer et al. . |
| 5,059,603 | 10/1991 | Rubin . |
| 5,087,631 | 2/1992 | Shaffer et al. . |
| 5,087,671 | 2/1992 | Loeppky et al. . |
| 5,094,815 | 3/1992 | Conboy et al. . |
| 5,155,137 | 10/1992 | Keefer et al. . |
| 5,212,204 | 5/1993 | Keefer et al. . |
| 5,234,956 | 8/1993 | Lipton . |
| 5,242,391 | 9/1993 | Place et al. . |
| 5,366,997 | 11/1994 | Keefer et al. . |
| 5,380,758 | 1/1995 | Stamler et al. . |
| 5,389,675 | 2/1995 | Christodoulou et al. . |
| 5,405,919 * | 4/1995 | Keefer et al. .................... 525/377 |
| 5,427,797 | 6/1995 | Frostell et al. . |
| 5,439,938 | 8/1995 | Snyder et al. . |
| 5,482,039 * | 1/1996 | Place ................................ 604/517 |
| 5,910,316 * | 6/1999 | Keefer et al. .................... 424/433 |

OTHER PUBLICATIONS

Andrews et al., *Gastroenterology*, 104, A33 (1993).
Aoki et al., *Am. J. Physiol.*, 258, G275–G281 (1990).
Artysbasheva et al., translated from *Zhurnal Organicheskoi Khimii* (J. Organic Chemistry–U.S.S.R.), 28, (6) 1168–1173 (1987).
Beckman et al., *Proc. Natl. Acad. Sci. USA*, 87, 1620–1624 (1990).
Beckman, *Nature*, 345, 27–28 (1990).
Beckman, *J. Development Physiol.*, 15, 53–59 (1991).
Bedford et al., *Br. J. Radiol.*, 39, 896–900 (1966).
Birckenbach et al., *Aus. D. Chem. Institut D. Betgakademie Clausthal*, Eingegaugen am 9, (1932).
Bohn et al., *J. Cardiovasc. Pharmacol.*, 14, S6–S12 (1989).
Bonakdar et al., *Calanta*, 36, 219–225 (1989).
Burnett et al., *Science*, 257, 401–404 (Jul. 17, 1992).
Coleman et al., *Int. J. Radiat. Oncol. Biol. Phys.*, 12, 1105–1108 (1986).
Dawson et al., *Proc. Natl. Acad. Sci. USA*, 88, 7797–7801 (1991).
DeFeudis, *Drugs of Today*, 24, (2), 103–115 (1988).
DeGraff et al., *I. J. Radiation Oncology Biol. Phys.*, 16, 1021–1024 (1989).
DeLuca et al., *Pharmaceutics and Pharmacy Practice* (Banker et al., eds.), 238–250 (J.B. Lippincott Co., Philadelphia, PA) (1982).
Drago et al., *J. Am. Chem. Soc.*, 83, 1819–1822 (1961).
Drago, *Free Radicals in Organic Chemistry*, Advances in Chemistry Series No. 36, 143–149 (American Chemical Society, Washington, DC) (1962).
Fast et al., *J. Leukocyte Biol.*, 52, 255–261 (1992).
Feelisch et al., *J. Cardiovasc. Pharmacol.*, 14, S13–S22 (1989).
Feelisch, *J. Cardiovasc. Pharmacol.*, 17, S25–S33 (1991).
Feldman et al., *Chemical & Engineering News*, 71, 26–38 (1993).
Filep et al., *Br. J. Pharmacol.*, 108, 323–326 (1993).
Fujitsuka et al., *Chem. Abstracts*, 82, 31108P (1975).
Furchgott, *Ann. Rev. Pharmacol. Toxicol.*, 24, 175–97 (1984).
Gambassi et al., "Ischemia–Reperfusion Injury and Histamine Release in Isolated Perfused Guinea–Pig Heart: Effects of Nitric Oxide Generators," *Pharmacological Research*, 25, 11–12 (1992).
Garg et al., *Biochem. and Biophys. Res. Comm.*, 171, 474–479 (1990).
Gatenby et al., *I. J. Radiation Oncology Biol. Phys.*, 14, 831–838 (1988).
Gehlen et al., *Berichte d. D. Chem. Gesellschaft*, LXV, 1130–1140 (1932). ("Reactions and properties of nitric oxide and its compounds. II. The salts of the nitric oxide compound of sulfurous acid," Chemical Abstracts, 26, 4764–65.).
Gelvan et al., *Proc. Natl. Acad. Sci. USA*, 88, 4680–4684 (1991).
Gillespie et al., *Br. J. Pharmacol.*, 97, 453P (1989).
Granger, *Am. J. Physiol.*, 255, H1269–H1275 (1988).
Hall et al., *Br. J. Radiol.*, 39, 302–307 (1966).
Hall, *Radiobiology for the Radiologist* (4th ed.), 133–164 (J.P. Lippincott Co., Philadelphia) (1994).
Halliwell et al., *FEBS*, 307, 108–112 (1992).
Halliwell et al., *Arch. Biochem. and Biophys.*, 246, 501–514 (1986).
Halliwell et al., *Biochem. J.*, 219, 1–14 (1984).
Hanbauer et al., *Neuroreport*, 3, 409–412 (1992).
Hansen et al., *N–Nitroso Compounds: Occurrence and Biological Effects*, IARC Scientific Publications No. 41, 21–29 (International Agency for Research on Cancer, Lyon, France) (1982).
Hibbs et al., *Biochem. and Biophys. Res. Comm.*, 157, 87–94 (1988).
Holford et al., *Clinical Pharmacokinetics*, 6, 429–453 (1981).
Holmquist et al., *Acta Physiol. Scand.*, 141, 441–442 (1991).
Holmquist et al., *Acta Physiol. Scand.*, 143, 299–304 (1991).
Howard–Flanders, *Nature*, 180, 1991–1192 (1957).
Hrabie et al., *J. Org. Chem.*, 58, 1472–1476 (1993).
Hutcheson et al., *Br. J. Pharmacol.*, 101, 815–820 (1990).
Ignarro et al., *J. Pharmacol. Exp. Ther.*, 218, 739–749 (1981).
Ignarro et al., *Ann. Rev. Pharmacol. Toxicol.*, 25, 171–191 (1985).
Ignarro et al., *Biochemical and Biophysical Research Communications*, 170, 2: 843–850 (Jul. 31, 1990).
Ignarro et al., *Nature*, 347, 131–132 (Sep. 13, 1990).
Ignarro, *Ann. Rev. Pharmacol. Toxicol.*, 30, 535–60 (1990).
Ignarro, *The FASEB Journal*, 3, 31–36 (1989).
Ignarro, *Hypertension*, 16, 477–483 (1990).
Imlay et al., *Science*, 240, 640–642 (1988).
Ischiropoulos et al., *Arch. Biochem. and Biophys.*, 298, 431–437 (1992).
Jaeschke et al., *Life Sciences*, 50, 1797–1804 (1992).
Jones, "Metastable Polymers of the Nitrogen Oxides. 1. Open Chain Nitric Oxide Analogues of Polythlazyl: A MNDO/AM1 Study," *J. Phys. Chem.*, 95, 2588–2595 (1991).
Kanner et al., *Archives of Biochemistry and Biophysics*, 289, 130–136 (1991).

Keefer et al., *Biology of Nitric Oxide, 2, Enzymology, Biochemistry, Immunology*, (Moncada et al., eds.), 153–156 (Portland Press, Chapel Hill, NC) (1992).
Kiedrowski et al., *Molecular Pharmacology*, 41, 779–784 (1992).
Kim et al., *J. Clin. Invest.*, 88, 112–118 (Jul. 1991).
Kruszyna et al., *Toxicol. Appl. Pharmacol.*, 91, 429–438 (1987).
Kubes et al., *Am. J. Physiol.*, 262, H611–H615 (1992).
Kubes et al., *Gastroenterology*, 104, A728 (1993).
Kubes et al., *Proc. Natl. Acad. Sci. USA*, 88, 4651–4655 (1991).
Kuhn et al., *J. Cardiovasc. Pharmacol.*, 14 (Suppl. 11), S47–S54 (1989).
Kuznetsov et al., *J. Mol. Struct.*, 263, 329–341 (1991).
Kwon et al., *J. Exp. Med.*, 174 (4) 761–767 (1991).
Lafon–Cazal et al., *Nature*, 364, 535–537 (1993).
Lefer et al., *Ann. Rev. Pharmacol. Toxicol.*, 33, 71–90 (1993).
Linz et al., *J. Mol. Cell Cardiol.*, 24, 909–919 (1992).
Lipton et al., *Nature*, 364, 626–631 (1993).
Longhi et al., *Inorg. Chem.*, 2, 85–88 (1963).
Lutz et al., *J.C.S. Chem. Comm.*, 247 (1977).
Maragos et al., *J. Med. Chem.*, 34, 3242–3247 (1991).
Maragos et al., *Cancer Res.*, 53 (3), 564–568 (1993).
Marletta et al., *BioFactors*, 2, 219–225 (1990).
Marmo et al., *Biomed. Biochim. Acta*, 43, 509–515 (1984).
Masini et al., *Int. Arch. Allergy Appl. Immunol*, 94, 257–258 (1991).
Masini et al., *Agents and Actions*, 33, 53–56 (1991).
Middleton et al., *J. Chem. Soc. Dalton*, 1898–1905, (1981).
Minotti et al., *J. Biol. Chem.*, 262, 1098–1004 (1987).
Mitchell et al., *Biochemistry*, 29, 2802–2807 (1990).
Mitchell et al., *Radiation Research*, 96, 422–428 (1983).
Morikawa et al., *Am. J. Physiol.*, 263, H1632–H1635 (1992).
Morley et al., *J. Cardiovasc. Pharmacol.*, 21, 670–676 (1993).
Murayama et al., *Int. J. Radiat. Biol.*, 44, 497–503 (1983).
Myers et al., *Nature*, 345, 161–163 (1990).
Nakanishi et al., *J.C.S. Chem. Comm.*, (1977).
Palmer et al., *Nature*, 327, 324–327 (1987).
Park et al., *Pharmaceut. Res.*, 9, 37–39 (1992).
Phillips et al., *Cancer Treatment Reports*, 68, 291–302 (1984).
Phillips et al., *I. J. Radiation Oncology Biol. Phys.*, 12, 1627–1635 (1986).
Pickard et al., *Br. J. Pharmacol.*, 104, 755–759 (1991).
Powers et al., *Nature*, 197, 710–711 (1963).
Radi et al., *Arch. Biochem. and Biophys.*, 288, 481–487 (1991).
Radomski et al., *The Lancet*, 1057–1058 (1987).
Rajfer et al., *The New England Journal of Medicine*, 326, 2:90–94 (Jan. 9, 1992).
Rubanyi et al., *Biochem. and Biophys. Res. Comm.*, 181, 1392–1397 (1991).
Russo et al., *Radiation Research*, 103, 232–239 (1985).
Saavedra et al., *J. Org. Chem.*, 57, 6134–6138 (1992).
Saran et al., *Free Rad. Res. Comm.*, 10, 221–226 (1990).
Siegfried et al., *Am. J. Physiol.*, 263, H771–H777 (1992).
Siemann et al., *Br. J. Cancer*, 58, 296–300 (1988).
Sjöstrand et al., *Acta Physiol. Scand.*, 140, 297–298 (1990).
Smith et al., *Gastroenterology*, 102 (Part 2), A516 (1992).
Smith et al., *Advances in Experimental Medicine and Biology*, 283, *Biological Reactive* Intermediates IV (Witmer et al., eds.), 365–369 (Plenum Press, New York, NY) (1991).
Stamler et al., *Proc. Natl. Acad. Sci. USA*, 89, 7674–7677 (1992).
Stamler et al., *Proc. Natl. Acad. Sci. USA*, 89, 444–448 (1992).
Stroh, *Science News*, 142, 10–11 (Jul. 4, 1992).
Stuehr et al., *J. Exp. Med.*, 169, 1543–1555 (1989).
Thomlinson et al., *Br. J. Cancer*, IX, 539–549 (1955).
Trissel, *Handbook on Injectable Drugs* (4th ed.), 622–629 (American Society of Hospital Pharmacists, Bethesda, MD) (1986).
von Sonntag, *The Chemical Basis of Radiation Biology*, pp. 31–56 and 295–352 (Taylor & Francis, London) (1987).
Weitz et al., *Berichte d. D. Chem. Gesellschaft*, LXVI, 1718–1727 (1933). ("Nitrosylsulfuric acid," Chemical Abstracts, 28, 2636.).
WHO Task Group on Environmental Health Criteria for Oxides of Nitrogen, *Environmental* Health Criteria 4: Oxides of Nitrogen, (World Health Organization, Geneva) (1977).
Wiersdorff et al., "N–aryl–N–nitrosohydroxylamine salts," Chem. Abstracts, 77, 48034f (1972).
Wilcox et al., *Chem. Res. Toxicol.*, 3, 71–76 (1990).
Wink et al., *Science*, 254, 1001–1003 (1991).
Woditsch et al., *Am. J. Physiol.*, 263, H1390–H1396 (1992).
Wood et al., *Biochem. and Biophys. Res. Comm.*, 192, 505–510 (1993).
Zhu et al., *Arch. of Biochem. and Biophy.*, 298, 452–457 (1992).

* cited by examiner

USE OF NITRIC OXIDE-RELEASING AGENTS TO TREAT IMPOTENCY

This appln is a div of 08/419,044 Apr. 10, 1995 U.S. Pat. No. 5,910,316 which is a continuation-in-part of U.S. patent application Ser. No. 08/121,169, filed Sep. 14, 1993, now U.S. Pat. No. 5,525,357 which issued Jun. 11, 1996 and which, in turn, is a continuation-in-part of U.S. application Ser. No. 07/935,565, filed Aug. 24, 1992, now U.S. Pat. No. 5,405,919. The entire disclosures of the U.S. Pat. No. 5,528,357 and the '565 application are incorporated herein by reference.

TECHNICAL FIELD OF THE INVENTION

The present invention relates to a method of treating impotency in a male, and more particularly, to the use of certain nitric oxide-releasing agents to treat impotency. The present invention also relates to nitric oxide delivery means comprising nitric oxide-releasing agents for use in the method.

BACKGROUND OF THE INVENTION

It is estimated that in the United States alone, there are between 10 and 20 million men with moderate to severe forms of erectile dysfunction. An additional 10 million men exist for whom urinary tract dysfunction is also a significant problem.

Penile erection and detumescence involve a complex interaction of direct neuronal activation combined with the release of endothelial derived contractile and relaxant factors. A variety of neurotransmitter substances and vasoactive modulators have been described. Of these, nitric oxide appears to play a primary role in the development of an erection.

Cavernosal smooth muscle relaxation is one of the primary events in penile erection. Although it is believed to be initiated by the synthesis and release of NO from nonadrenergic-noncholinergic neurons of the corpus cavernosum (Kimura et al., Nippon Hinyokika Gakkai Zasshi 84(9): 1660–1664 (1993); Rajfer et al., N. Engl. J. Med. 326(2): 90–94 (1992); Knispel et al., Urol. Res. 20(4): 253–257 (1992); Burnett et al., Science 257(5068): 401–403 (1992); and Mills et al., Biol. Reprod. 46(3): 342–348 (1992)), studies undertaken to determine whether or not the serum levels of NO metabolites, i.e, nitrites and nitrates, increase in peripheral and cavernosal blood during penile erection in potent adult humans demonstrated that nitrite and nitrate levels do not change appreciably during and immediately following erection (Moriel et al., Urology 42(5): 551–553 (1993)). Physiological concentrations of oxygen in the corpus cavernosum tissue, however, are believed to modulate penile erection by regulating NO synthesis (Kim et al., J. Clin. Invest. 91(2): 437–442 (1993)). It has been further hypothesized that relaxation of the corpus cavernosum, initiated in response to nitric oxide synthesis and release from nonadrenergic-noncholinergic neurons, could be amplified and maintained by NO production as a result of platelet trapping in the corpus cavernosum during the first phase of penile erection (Alberti et al., Minerva Urol. Nefrol. 45(2): 49–54 (1993)).

Currently available therapies for erectile dysfunction include needle injection of a vasodilator drugs directly into the penis; a vacuum constriction device (VCD), which pulls blood into the penis and holds it there with a constriction ring; a surgical implant, which provides rigidity; oral medication, such as yohimbine, which appears to have beneficial effects in only a small proportion of patients; psychological therapy, for which few data exist on long term benefit; and vascular surgery, which is appropriate in only a very small number of patients. All six therapies have significant drawbacks. In fact, they are so limited in appeal that fewer than ten percent of men with erectile dysfunction have adopted any one of the therapies at all. In addition, each of these therapies suffers from exceedingly high rates of discontinuance for reasons that are not entirely related to the therapy, itself. There remains a need, therefore, for an effective method of treating impotency.

Nitric oxide has been utilized as a means of studying penile erection and penile dysfunction due to diabetes and venous leakage, for example. The potential usefulness of nitric oxide to treat impotence has been discussed by McGuffey (Am. Pharm. NS33(7): 20 (1993)).

Nitric oxide in its pure form, however, is a highly reactive gas having limited solubility in aqueous media (WHO Task Group on Environmental Health Criteria for Oxides of Nitrogen, Oxides of Nitrogen, Environmental Health Criteria 4 (World Health Organization: Geneva, 1977)). Nitric oxide, therefore, is difficult to introduce reliably into most biological systems without premature decomposition.

A number of compounds have been developed that are capable of delivering nitric oxide in a pharmacologically useful way. Such compounds include compounds that release nitric oxide upon being metabolized and compounds that release nitric oxide spontaneously in aqueous solution.

Compounds that release nitric oxide upon being metabolized include the widely used nitrovasodilators glyceryl trinitrate and sodium nitroprusside (SNP) (Ignarro et al., J. Pharmacol. Exp. Ther., 218, 739–749 (1981); Ignarro, Annu. Rev. Pharmacol. Toxicol., 30, 535–560 (1990); Kruszyna et al., Toxicol. Apol. Pharmacol., 91, 429–438 (1987); Wilcox et al., Chem. Res. Toxicol., 3, 71–76 (1990)), which are relatively stable but release nitric oxide on activation. While this feature may be an advantage in some applications, it also can be a significant liability. For example, tolerance to glyceryl trinitrate can develop via the exhaustion of the relevant enzyme/cofactor system (Ignarro et al., Annu. Rev. Pharmacol. Toxicol., 25, 171–191 (1985); Kuhn et al., J. Cardiovasc. Pharmacol., 14 (Suppl. 11), S47–S54 (1989)). Also, prolonged administration of nitroprusside results in the metabolic production of cyanide, which leads to toxicity (Smith et al., "A Potpourri of Biologically Reactive Intermediates" in Biological Reactive Intermediates IV. Molecular and Cellular Effects and Their Impact on Human Health (Witmer et al., eds.), Advances in Experimental Medicine and Biology Volume 283 (Plenum Press: New York, 1991), pp. 365–369). S-Nitroso-N-acetylpenicillamine (SNAP) has been reported to release nitric oxide in solution and to be effective at inhibiting DNA synthesis (Garg et al., Biochem. and Biophys. Res. Comm., 171, 474–479 (1990)).

SNP has been administered to primates for purposes of studying the physiology and pharmacology of erection (Hellstrom et al., J. Urol. 151(60: 1723–1727 (1994)). Intracavernosal injection of SNP induced erections with dose-dependent increases in cavernosal pressure and penile length.

The NO donor linsidomine chlorohydrate, otherwise known as 3-morpholinosydnonimine or SIN-1, was administered to 30 human patients with erectile dysfunction caused by venous leakage (Wegner et al., Urology 42(4): 409–411 (1993)) and was less effective than prostaglandin E1 (PGE1) in treating the dysfunction in over two-thirds of the patients treated. SIN-1 was also found to be less effective than SNP in relaxing isolated rabbit corpus cavernosum (Holmquist et al., J. Urol. 150(4): 1310–1315 (1993)). More promising results with SIN-1 were obtained in a 63-patient study carried out by Stief et al. (J. Urol. 148(5): 1437–1440 (1992)). However, activation of SIN-1 by oxygen produces both NO and superoxide ion, two species that can combine with one another to produce the potent oxidant, $ONOO^-$. The potential to produce this toxic by-product is believed to limit the utility of such sydnonimine drugs.

Numerous nitric oxide-nucleophile complexes also have been described, e.g., by Drago, *ACS Adv. Chem. Ser.*, 36, 143–149 (1962). See also Longhi and Drago, Inorg. Chem., 2, 85 (1963). Some of these complexes, known as NONOates, evolve nitric oxide on heating or hydrolysis (Maragos et al., *J. Med. Chem.*, 34, 3242–3247 (1991)).

These compounds contain the anionic $N_2O_2^-$ group or derivatives thereof. Many of these compounds have proven especially promising pharmacologically because, unlike SNP and nitroglycerin, they release NO without first having to be activated. The only other series of drugs currently known to be capable of releasing NO purely spontaneously is the S-nitrosothiol series, compounds of structure R—S—N=O (Stamler et al., *Proc. Natl. Acad. Sci. U.S.A.*, 89, 444–448 (1992)); however, the R—S—N=O→NO reaction can be kinetically complicated and difficult to control (Morley et al., *J. Cardiovasc. Pharmacol.*, 21, 670–676 (1993)), and extensive redox activation (McAninly et al., J. Chem. Soc., *Chem. Comm.*, 1758–1759 (1993)) and metabolism (Kowaluk et al., *J. Pharmacol. Exp. Ther.*, 255, 1256–1264 (1990)) have been documented for these compounds. Moreover, the oxidation state of nitrogen in the S-nitrosothiols is +3, rather than the +2 of nitric oxide. While variation in the R group of the R—S—N=O compounds provides a means of altering their chemical, and hence pharmacological, properties, the NONOate series is especially versatile in this respect. NONOates having reproducible half-lives ranging from 2 seconds to 20 hours have been prepared. They can be O-alkylated to provide either spontaneous NO-generators with half-lives of up to a week or more or prodrugs that cannot release NO at all until the oxygen substituent is removed metabolically. The NONOate function can be coordinated via the two oxygen atoms to metal centers; it can be attached to natural products, such as spermine (a constituent of human semen) and peptides; and it can be bound in solid polymeric matrices to provide a point source of NO. A compound containing more than one nucleophile residue (such as, for example, the polyamine, spermine) can be bound to more than one NONOate group, to thereby provide a single NONOate molecule with bi- or polyphasic NO release rates. By providing such a wide variety of NO release rates, physical forms, and potential strategies for targeting NO delivery to specific sites in the body, the NONOates constitute a most advantageous series of compounds on which to base NO donor drug development efforts.

Nitric oxide/nucleophile complexes (NONOates) that release nitric oxide in aqueous solution are disclosed in U.S. Patent Nos. 4,954,526, 5,039,705, 5,155,137, 5,185,376, 5,208,233, 5,212,204, 5,250,550, 5,366,977, and 5,389,675, as being useful cardiovascular agents (see also Maragos et al., *J. Med. Chem.*, 34, 3242–3247 (1991)).

Despite the promise of the nitric oxide/nucleophile complexes that have been described thus far in the literature, their pharmacological application is limited by their tendency to distribute evenly throughout the medium. Such even distribution is a great advantage in many applications, but tends to compromise their selectivity of action. However, the nitric oxide/nucleophile complexes can be incorporated into polymers in order to overcome this limitation by enabling concentrated and localized release of NO at a given site in a controllable and predictable manner such that effective dosing can be realized. This imparts a tremendous advantage to the technology for the treatment of erectile dysfunction.

The present invention provides a method of treatment for impotency in a male animal that overcomes the above-described disadvantages of currently available treatment methods by employing NONOates as nitric oxide-releasing agents in the form of polymers, pharmaceutical compositions, and various delivery means comprising such compositions and polymers. Accordingly, the present invention also seeks to provide delivery means for use in the present inventive method. These and other objects and advantages of the present invention, as well as additional inventive features, will be apparent from the description of the invention provided herein.

SUMMARY OF THE INVENTION

The present invention provides a method of treatment for impotency in a male animal, including a human. The method comprises the administration of a nitric oxide-releasing agent, which is capable of providing a penile erection-inducing amount of nitric oxide to the male animal and which includes a nitric oxide-releasing $[N_2O_2]$ functional group. The nitric oxide-releasing agent can be a compound comprising a nitric oxide-releasing $[N_2O_2]$ functional group, it can be a polymer to which is bound a nitric oxide-releasing $[N_2O_2]$ functional group, or it can be a delivery means, e.g., a transurethral applicator, penile implant, dermal patch or condom, comprising such a compound or polymer. In accordance with the method of the present invention, the nitric oxide-releasing agent provides NO to the penis of an impotent male animal in an amount sufficient to cause a penile erection.

In keeping with the invention, the delivery means can be coated with or made of a nitric oxide-releasing agent in the form of a polymer and enables the controllable and predictable release of NO to the penis in such a manner that effective therapeutic dosing of impotency is realized. The delivery means can be biodegradable. Delivery means comprising the nitric oxide-releasing agent are also provided.

DETAILED DESCRIPTION OF THE INVENTION

Figure 1:
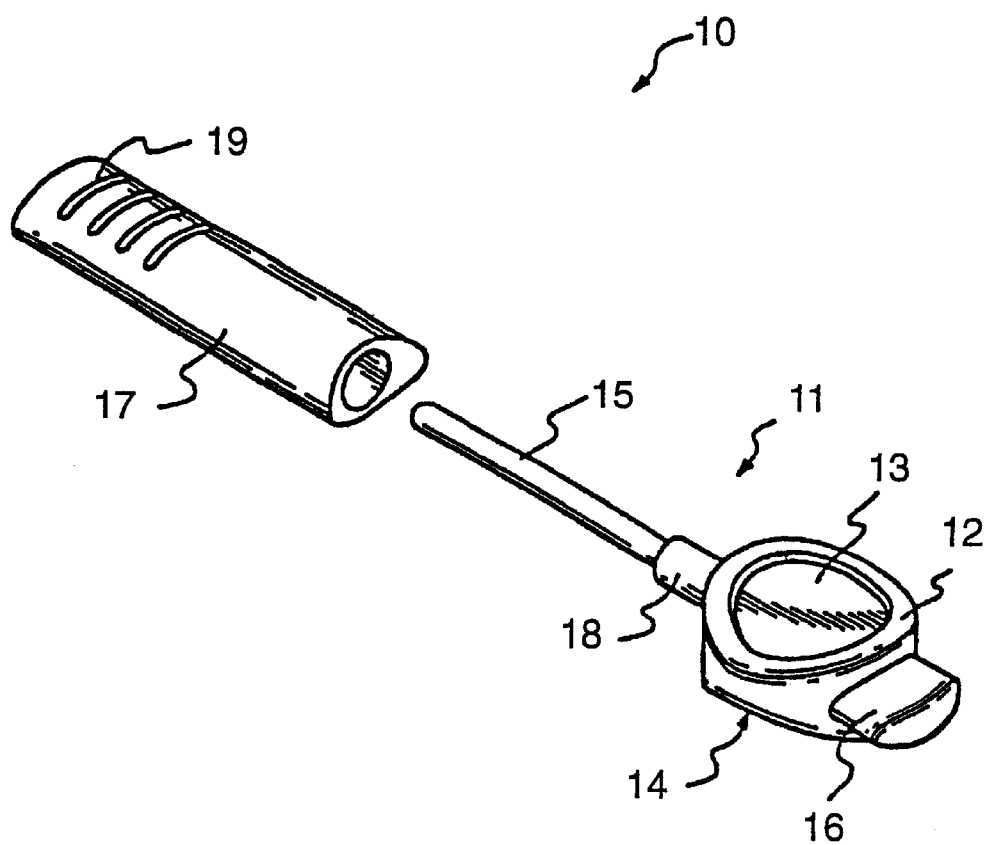
FIG. 1 illustrates an exploded view of one embodiment of a transurethral therapeutic device for delivery of the nitric oxide-releasing agent to the urethra.

The present invention provides a method for the treatment of impotency in a male animal, including a human. The method involves the administration to a male. animal, in particular a human, of a nitric oxide-releasing agent. The nitric oxide-releasing agent can be a compound comprising a nitric oxide-releasing $[N_2O_2]$ functional group or a polymer to which is bound a nitric oxide-releasing $[N_2O_2]$ functional group or a delivery means, such as a transurethral applicator, a penile implant, a dermal patch or a condom, comprising such a compound or polymer. "Bound to a polymer" means that the [$N_2O_2$] functional group is associated with, part of, incorporated with or contained within the polymeric matrix either physically or chemically. Physical association or bonding of the $N_2O_2^-$ functional group to the polymer may be achieved by coprecipitation of the polymer with a nitric oxide/nucleophile complex as well as by covalent bonding of the $N_2O_2^-$ group to the polymer. Chemical bonding of the $N_2O_2^-$ functional group to the polymer may be by, for example, covalent bonding of the nucleophile moiety of the nitric oxide/nucleophile adduct to the polymer such that the nucleophile residue to which the $N_2O_2^-$ group is attached forms part of the polymer itself, i.e., is in the polymer backbone or is attached to pendant groups on the polymer backbone. The manner in which the nitric oxide-releasing $N_2O_2^-$ functional group is associated, part of, or incorporated with or contained within, i.e., "bound," to the polymer is inconsequential to the present invention and all means of association, incorporation and bonding are contemplated herein.

The delivery means can be coated with or made of a nitric oxide-releasing agent in the form of a polymer and enables the controllable and predictable release of NO to the penis in such a manner that effective therapeutic dosing of impotency is realized. "Nitric oxide delivery means" is meant to include the many forms in which the nitric oxide-releasing agent can be configured, such as a transurethral applicator, an implant, drug pump, catheter, self-adhering means, liposome, microparticle, solution, microsphere, bead, disk or other pharmaceutical composition as described more fully below. The delivery means can be biodegradable.

The nitric oxide-releasing agent provides NO to the penis of an impotent male animal in an amount sufficient to cause a penile erection. Determination of what amount is sufficient to induce a penile erection is as described below with respect to dosages. Whether or not a particular animal suffers from impotency is readily determined. Whether or not a particular animal is at risk for impotency can be assessed by those of skill in the art by taking into account known risk factors. Factors such as diabetes mellitus or venous leakage are likely to place a man at risk for impotency.

The present invention also provides various nitric oxide delivery means for use in the present inventive method as described more fully below.

The nitric oxide-releasing [$N_2O_2$] functional group is X—[N(O)NO] or [N(O)NO]—X, wherein X is an organic or inorganic moiety bonded to the —[N(O)NO] or [N(O)NO]— functional group. The compound containing the [$N_2O_2$] functional group can be incorporated into or be part of a polymer. The [$N_2O_2$] group can be covalently bonded in the polymer by way of the moiety X. Incorporation of the $N_2O_2^-$ functional group into a polymer enables localized release of NO to the penis. "Localized release" means into or adjacent to the corpus cavernosum. Localized release enhances the selectivity of action of the nitric oxide-releasing [$N_2O_2$] functional group. If [$N_2O_2$] functional groups attached to the polymer are localized, then the effect of their NO release will be concentrated in the tissues with which they are in contact. If the polymer is soluble, selectivity of action can still be arranged, for example, by attachment to or derivatization of an antibody specific to the target tissue. Similarly, attachment of [$N_2O_2$] functional groups to small peptides that mimic the recognition sequences of ligands for important receptors provides localized, concentrated NO release, as would attachment to oligonucleotides capable of site-specific interactions with target sequences in a nucleic acid.

Additionally, incorporation of the [$N_2O_2$] functional group into a polymer can reduce the propensity of the nitric oxide/nucleophile adduct for the relatively rapid release of NO. This prolongs the release of NO by the [$N_2O_2$] functional group, and allows for efficient dosing to achieve a penile erection and, possibly, concomitant reduction in the frequency of dosing.

While not being bound to any particular theory, it is believed that longevity of nitric oxide release in the polymer-bound nitric oxide/nucleophile adduct compositions of the present invention is to be attributed both to the physical structure of the composition and to electrostatic effects. Thus, it is believed that if the polymer is an insoluble solid, $N_2O_2^-$ groups near the surface of the particle should be available for rapid release while those that are more deeply imbedded are sterically shielded, requiring more time and/or energy for the nitric oxide to work its way into the medium. Unexpectedly, it has been found that increasing positive charge in the vicinity of an $N_2O_2^-$ functional group also tends to increase the halflife of nitric oxide generation. The mechanism of this rate retardation may be attributable simply to repulsive electrostatic interactions, i.e., increasing the number of $H^+$-repelling positive charges in the vicinity of the $N_2O_2^-$ groups inhibits attack of positively charged $H^+$ ions on the $N_2O_2^-$ functional group and slows the rate of its $H^+$-catalyzed decomposition. For example, by attaching amino groups to the polymeric support that are capable of forming the nitric oxide-releasing $N_2O_2^-$ functional group on reaction with nitric oxide, partially converted structures can be produced on less-than-exhaustive treatment with nitric oxide that after exposure to water contain a large number of positively charged ammonium centers surrounding the $N_2O_2^-$ group that electrostatically inhibit the approach of $H^+$ ions capable of initiating nitric oxide loss from the nitric oxide releasing $N_2O_2^-$ functional group.

The nitric oxide-releasing [$N_2O_2$] functional groups that are bound to the polymer generally are capable of releasing NO in an aqueous environment spontaneously upon contacting an aqueous environment, i.e., they do not require activation through a redox reaction or electron transfer, such as is required for glyceryl trinitrate and SNP. Some of the nitric oxide/nucleophile complexes useful in the context of the present invention do require activation by particular means, but only as necessary to free the nitric oxide-releasing X—[N(O)NO]$^-$ group in the vicinity of the penis or corpus cavernosum. As an example, covalent attachment of a protecting group to the anionic [N(O)NO]$^-$ function provides a means of postponing NO release until the molecule reaches the penis, where cells/tissues are capable of metabolically removing the protecting group. While the polymer-bound, nitric oxide-releasing compositions of the present invention are capable of releasing NO in an aqueous solution, such a polymer preferably releases NO under physiological conditions.

The nitric oxide-releasing [$N_2O_2$] functional group is preferably a nitric oxide/nucleophile adduct, i.e., a complex of NO and a nucleophile, most preferably a nitric oxide/nucleophile complex which contains the anionic moiety X—[N(O)NO]$^-$, wherein X is any suitable nucleophile residue. The nucleophile residue is preferably that of a primary amine (e.g., X=$(CH_3)_2CHNH$, as in $(CH_3)_2CHNH[N(O)NO]Na$), a secondary amine (e.g., X=$(CH_3CH_2)_2N$, as in $(CH_3CH_2)_2N[N(O)NO]Na$), a polyamine (e.g., X=spermine, as in the zwitterion $H_2N(CH_2)_3NH_2^+(CH_2)_4N[N(O)NO]^-(CH_2)_3NH_2$, X=(ethylamino)ethylamine, as in the zwitterion $CH_3CH_2N[N(O)NO]^-CH_2CH_2NH_3^+$, or X=3-(n-propylamino)propylamine, as in the zwitterion $CH_3CH_2CH_2N[N(O)NO]^-CH_2CH_2CH_2NH_3^+$), or oxide (i.e., X=$O^-$, as in $NaO[N(O)NO]Na$), or a derivative thereof.

Such nitric oxide/nucleophile complexes are stable solids and are capable of delivering NO in a biologically usable form at a predictable rate.

The nucleophile residue is preferably not an entity such as that of sulfite (e.g., $X=SO_3^-$, as in $NH_4O_3S[N(O)NO]NH_4$) even though the complex is a stable compound, since it is capable of releasing NO in an aqueous environment only under harsh, nonphysiological conditions.

Other suitable nitric oxide/nucleophile complexes include those having the following formulas:

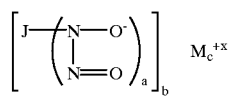
(I)

wherein J is an organic or inorganic moiety, including, for example, a moiety which is not linked to the nitrogen of the $[N_2O_2]$ group through a carbon atom, $M^{+x}$ is a pharmaceutically acceptable cation, where x is the valence of the cation, a is 1 or 2, and b and c are the smallest integers that result in a neutral compound, preferably such that the compound is not a salt of alanosine or dopastin, as described in U.S. Pat. No. 5,212,204, incorporated herein by reference;

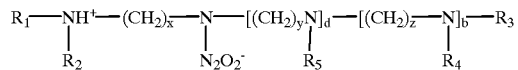
(II)

wherein b and d are the same or different and may be zero or one, $R_1$, $R_2$, $R_3$, $R_4$, and $R_5$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12, as described in U.S. Pat. No. 5,155,137, incorporated herein by reference;

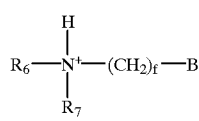
(III)

wherein B is

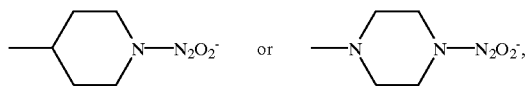

$R_6$ and $R_7$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, f is an integer from 0 to 12, with the proviso that when B is the substituted piperazine moiety

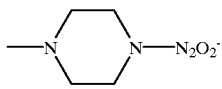

then f is an integer from 2 to 12, as described in U.S. Pat. No. 5,250,550 incorporated herein by reference;

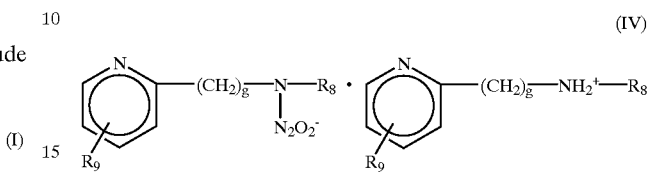
(IV)

wherein $R_8$ is hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, $R_9$ is hydrogen or a $C_1$–$C_{12}$ straight or branched chain alkyl, and g is 2 to 6, as described in U.S. Pat. No. 5,250,550, incorporated herein by reference;

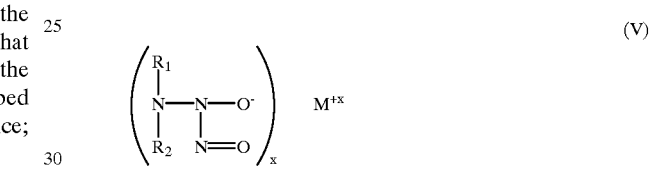
(V)

wherein $R_1$ and $R_2$ are independently selected from the group consisting of a straight chain or branched chain $C_1$–$C_{12}$ alkyl group and a benzyl group, preferably such that no branch occurs on the alpha carbon atom, or else $R_1$ and $R_2$, together with the nitrogen atom to which they are bonded, form a heterocyclic group, preferably a pyrrolidino, piperidino, piperazino or morpholino group, $M^{+x}$ is a pharmaceutically acceptable cation, and x is the valence of the cation, as described in U.S. Pat. Nos. 5,039,705 and 5,208,233 and U.S. patent application Ser. No. 08/017,270, filed Feb. 12, 1993, and incorporated herein by reference;

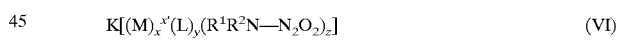
(VI)

wherein M is a pharmaceutically acceptable metal, or, where x is at least two, a mixture of two different pharmaceutically acceptable metals, L is a ligand different from ($R^1R^2N$—$N_2O_2$) and is bound to at least one metal, $R_1$ and $R^2$ are each organic moieties and may be the same or different (preferably where M is copper, x is one, L is methanol, and y is one, that at least one of $R^1$ or $R^2$ is not ethyl), x is an integer of from 1 to 10, x' is the formal oxidation state of the metal M, and is an integer of from 1 to 6, y is an integer of from 1 to 18, and where y is at least 2, the ligands L may be the same or different, z is an integer of from 1 to 20, and K is a pharmaceutically acceptable counterion to render the compound neutral to the extent necessary, as described in U.S. Pat. No. 5,389,675 and incorporated herein by reference;

(VII)

wherein R is $C_{2-8}$ lower alkyl, phenyl, benzyl, or $C_{3-8}$ cycoloalkyl, any of which R groups may be substituted by one to three substituents, which are the same or different, selected from the group consisting of halo, hydroxy, $C_{1-8}$ alkoxy, —$NH_2$, —$C(O)NH_2$, —$CH(O)$, —$C(O)OH$, and —$NO_2$, X is a pharmaceutically acceptable cation, a pharmaceutically acceptable metal center, or a pharmaceutically acceptable organic group selected from the group consisting of $C_{1-8}$ lower alkyl, —$C(O)CH_3$, and —$C(O)NH_2$, and y is one to three, consistent with the valence of X, as described in U.S. Pat. No. 4,954,526 and incorporated herein by reference; and

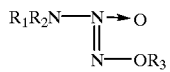

(VIII)

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$, together with the nitrogen atom to which they are bonded, form a heterocyclic group, preferably a pyrrolidino, piperidino, piperazino or morpholino group, and $R_3$ is a group selected from $C_{1-12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_{1-12}$ unsubstituted or substituted acyl, sulfonyl and carboxamido; or $R_3$ is a group of the formula —$(CH_2)_n$—$ON=N(O)NR_1R_2$, wherein n is an integer of 2–8, and $R_1$ and $R_2$ are as defined above; preferably $R_1$, $R_2$ and $R_3$ do not contain a halo or a hydroxy substituent α to a heteroatom, as described in U.S. Pat. No. 5,366,997.

Any of a wide variety of polymers can be used in the context of the present invention. It is only necessary that the polymer selected be biologically acceptable. Illustrative of polymers suitable for use in the present invention are polyolefins, such as polystyrene, polypropylene, polyethylene, polytetrafluoroethylene, polyvinylidene difluoride, polyvinylchloride, polyethyleneimine, and derivatives thereof; polyethers, such as polyethyleneglycol; polyesters, such as poly(lactide/glycolide); polyamides, such as nylon; polyurethanes; starburst dentrimers biopolymers, such as peptides or proteins (e.g., antibodies), nucleic acids (e.g., oligonucleotides), and the like.

The physical and structural characteristics of the polymers suitable for use in the present invention are not narrowly critical, but rather will depend on the route and frequency of administration. The polymer can be biodegradable.

The nitric oxide-releasing agents can be administered in a wide variety of forms of delivery means. Any delivery means should adequately protect the integrity of the No prior to its release and should control the release of the NO at such a rate, in such an amount, and in such a location as to serve as an effective means of treating the impotency. For example, delivery means for local administration or administration for localized release include, but are not limited to, a penile implant, a drug pump, a drug-delivery catheter (pressure-driven, iontophoretic or transurethral), a self-adhering means, a liposome, a microparticle, a microsphere, a bead, a condom, a dermal patch, a disk or other device. The advantages of local administration or localized release include the ability to attain effective concentrations of NO at the target site more quickly, the use of a smaller dose, and the realization of fewer toxic side effects than could occur on systemic administration and release. Delivery means for systemic administration for localized release include, but are not limited to, solutions, suspensions, emulsions, capsules, sachets, tablets, dermal (topical) patches, lozenges, aerosols, liposomes, microparticles, microspheres, beads, prodrugs, tissue-specific antibodies, small peptides that mimic ligand recognition sequences, and sequence-specific oligonucleotides as described above. The polymer, itself, may be structurally sufficient to serve as a form of delivery means. Alternatively, the polymer can be incorporated into or coated onto other matrices, substrates or the like, or can be microencapsulated or the like.

The nitric oxide-releasing [$N_2O_2$] functional groups, including the compounds described above, can be bound to a polymeric support in a number of different ways. For example, the compounds described above can be bound to the polymer by coprecipitation of such compounds with the polymer. Coprecipitation can involve, for example, solubilizing both the polymer and the nitric oxide/nucleophile compound and evaporating the solvent. Monomers containing the [$N_2O_2$] group also can be dissolved in molten polymer, which, upon solidification when the temperature is lowered, contains a rather uniform distribution of [$N_2O_2$] groups within the matrix.

The [$N_2O_2$] functional group can be attached to an atom in the backbone of the polymer, or it can be attached to a group pendant to the polymer backbone, or it can simply be entrapped in the polymeric matrix. Where the [$N_2O_2$] functional group is in the polymer backbone, the polymer includes, in its backbone, sites that are capable of reacting with NO to bind the NO for future release. For example, where the polymer is polyethyleneimine, the polymer includes nucleophilic nitrogen atoms, which react with No to form the [$N_2O_2$] functional group at the nitrogen in the backbone. Where the [$N_2O_2$] functional group is a group pendant to the polymer backbone, the polymer can contain, or be derivatized with, a suitable nucleophilic residue capable of reacting with NO to form the [$N_2O_2$] functionality. Reaction of the polymer that contains a suitable nucleophilic residue, or of the suitably derivatized polymer, with NO thus provides a polymer-bound nitric oxide-releasing [$N_2O_2$] functional group.

One skilled in the art will appreciate that suitable methods of administering the nitric oxide-releasing agents of the present invention to a male animal, including a human male, are available, and, although more than one route can be used to administer a particular compound or polymer, a particular route can provide a more immediate and more effective result than another route. Pharmaceutically acceptable carriers are also well-known to those who are skilled in the art. The choice of carrier for a pharmaceutical composition will be determined in part by the particular composition, as well as by the particular method used to administer the composition. Accordingly, there is a wide variety of suitable formulations of pharmaceutical compositions for use in the present invention.

Formulations suitable for oral administration can consist of (a) liquid solutions, such as an effective amount of the polymer-bound composition dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Transurethral administration of the drug is preferred, although not essential. The term "transurethral" is used to refer to delivery of the drug into the urethra, such that the drug contacts and passes through the wall of the urethra. As explained in co-pending U.S. patent application Ser. No. 07/514,397, entitled "Treatment of Erectile Dysfunction" (published internationally as WO91/16021), the disclosure of which is incorporated by reference herein, transurethral administration of a drug can be carried out in a number of different ways. For example, the drug can be introduced into the urethra from a flexible tube, squeeze bottle, pump or aerosol spray. The drug may also be contained in coatings, pellets or suppositories, which are absorbed, melted or bioeroded in the urethra. In certain embodiments, the drug is included in a coating on the exterior surface of a penile insert. A preferred drug delivery device for administering a drug transurethrally is shown in FIG. 1.

In FIG. 1, a transurethral drug delivery device is shown generally at 10. The device comprises a transurethral insert 11 having an easily graspable segment 12 that has opposing symmetrically concave surfaces 13 and 14 adapted to be held by two fingers. A drug is contained within the shaft 15, which is sized to fit within the urethra. A longitudinal plunger, the top of which is seen at 16, is slidably insertable into the longitudinal bore contained within shaft 15. To extrude a drug into the urethra, shaft 15 is inserted into the urethra, and plunger tip 16 is pushed into segment 12. The inserter 11 is then removed. Prior to use, and during storage, the device is capped with elongate cap 17, which fits snugly over flange 18 at the proximal end of shaft 15. The cap 17 is provided with a series of parallel ridges 19 to facilitate gripping of the cap and removal from inserter 11.

Although the configuration shown in FIG. 1 is a preferred configuration, other inserter/container configurations can be used and any mechanism by which a predetermined quantity of drug can be introduced from the inserter at a predetermined depth in the urethra is suitable for use with this invention. Examples of other such devices are those described and illustrated in WO91/16021, incorporated by reference above. The devices can either be manufactured under sterile conditions, thereby eliminating the need for post-manufacturing sterilization, or they can be manufactured under non-sterile conditions and then subsequently sterilized by any suitable technique, e.g., radiation sterilization. The devices can be manufactured by typical plastic forming and coating processes known in the art, including molding extrusion, heat forming, dip coating, and the like.

The drug also may be administered topically, transdermally or by any other available and effective means. Transdermal drug administration, as is well known to those skilled in the art, involves the delivery of a pharmaceutical agent via percutaneous passage of the drug into the systemic circulation of the patient. See Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1–3, Kydonieus and Berner (eds.), CRC Press (1987).

A variety of types of transdermal patches may be used in the method described herein. For example, a simple adhesive patch can be used which is prepared from a backing material and an acrylate adhesive. The adhesive layer is formulated so that a drug, and any carriers or enhancers to be used, are contained therein. Alternatively, a hydrogel matrix patch can be used in which a drug, water and, typically, hydrophilic polymers, are used to form a hydrogel, which is then incorporated into a transdermal patch between the backing and the adhesive layer. As will be appreciated by those skilled in the art, a number of other types of patch configurations can be used as well, including liquid reservoir patches, foam matrix patches, and the like. See, e.g., U.S. Pat. Nos. 3,598,122, 4,649,075 and 5,120,544, the disclosures of which are incorporated by reference herein.

Other components may be incorporated into such transdermal patches as well. For example, compositions and/or transdermal patches may be formulated with one or more preservatives or bacteriostatic agents, e.g., methyl hydroxybenzoate, propyl hydroxybenzoate, chlorocresol, benzalkonium chloride, or the like.

The dose administered to an animal, particularly a human, in the context of the present invention should be sufficient to effect a penile erection in the male over a reasonable time frame. The dose will be determined by the strength of the particular nitric oxide-releasing agent employed, the type of delivery means employed, the route of administration, the condition and weight of the animal to be treated, the timing of administration, i.e., with respect to sexual intercourse, frequency of administration, and the length of time of administration. The size of the dose also will be determined by the existence, nature, and extent of any adverse sideeffects that might accompany the administration of a particular composition or delivery means. A suitable dose, for example, is about 0.002 mg–100 mg of nitric oxide. The dose can be administered acutely or chronically, preferably acutely.

The following examples further illustrate the present invention, but do not limit the scope thereof.

EXAMPLE 1

This example illustrates the preparation of a polymerbound nitric oxide/nucleophile complex by coprecipitation of a monomeric form thereof with a polymer.

One gram of polymer [poly(lactide/glycolide, 50:50) from MediSorb] was dissolved in 2 ml of tetrahydrofuran. To the solution was added 300 mg of DETA/NO, $[H_2N(CH_2)_2]_2N-N_2O_2H$, zwitterionic form, and the mixture was stirred under an argon stream to remove solvent slowly until the mixture became too viscous to stir. The mixture was then placed in a vacuum oven (ca. 1 mm) at 30° C. for 5 hours to remove the residual solvent. The mixture was finally pressed on a carver press at 20,000 lbs. at 140° F. for 5 minutes. A 1"×1" film, 44 mils thick, was thus prepared. Using a chemiluminescence procedure as described in Maragos et al., *J. Med. Chem.*, 34, 3242–3247 (1991), nitric oxide was recovered from this polymer on treatment with acid at the rate of 8 nmol of NO per milligram of solid.

EXAMPLE 2

This example illustrates the preparation of a polymer-bound nitric oxide/nucleophile adduct in which the $N_2O_2^-$ functional group is bound directly to an atom in the polymer backbone.

A slurry of 10.0 g of polyethyleneimine on silica gel (Aldrich) in 150 ml of acetonitrile was stirred for 3 days under a NO pressure of 5 atm or 75–80 psig. The resulting orange solid was filtered, washed with acetonitrile and then ether, and dried in vacuo for 6 h. Using the chemiluminescence procedure identified in Example 1, it was determined that NO was recovered from this polymer on treatment with acid at the rate of 3 nmol/mg.

Control experiments with polymer that had not been exposed to NO produced no chemiluminescence signal.

EXAMPLE 3

This example illustrates the preparation of a polymer containing nitric oxide-releasing $N_2O_2^-$ groups that are attached to nucleophile residues pendant on the polymer backbone by the reaction of a primary amine with a derivatized polystyrene.

An aminostyrene polymer was prepared by warming 3.0 g of chloromethylated polystyrene (1% divinylbenzene; 1.09 mEq Cl per gram; 200–400 mesh; Polysciences, Inc., Warrington, Pa.) in 20 ml of n-propyl-1,3-propanediamine to 60° C. in an oil bath and swirling periodically for 5 days. The polymer was then filtered, washed repeatedly with water, then methanol and finally dichloromethane, and dried in vacuo for 24 h. Elemental analysis showed this material to be 2.21% nitrogen, indicating that approximately 80% of the chlorines had been replaced by propylpropanediamino groups.

A slurry of 1.0 g of the aminopolystyrene polymer in 50 ml of acetonitrile was placed under 5 atm of nitric oxide in a Parr apparatus and shaken intermittently for 3 days. The product was filtered and dried in vacuo to yield 0.84 g of cream colored polymer. The elemental analysis (C: 87.32; H: 8.00; N: 2.45) revealed that approximately one-third of the amino side chains became attached to $N_2O_2^-$ groups under these conditions.

Using the chemiluminescence procedure of Maragos et al. (vide supra), it was demonstrated that nitric oxide can be recovered from the $N_2O_2^-$ group-containing polymers described above.

EXAMPLE 4

This example illustrates the preparation of a polyethylene glycol-based NO-releasing polymer using two different methods of preparation. In both methods, the polymer-bound nitric oxide/nucleophile complex is formed by coprecipitation of a monomeric form of nitric-oxide/nucleophile compound with a polymer.

In one method, 20 mg of 1,1-diethyl-2-hydroxy-2-nitrosohydrazine sodium salt (DEA/NO) and 2.5 g of polyethylene glycol-1450 (Union Carbide) were dissolved in 25 ml of methanol. The homogeneous solution was placed on a rotary evaporator at 40° C. and the solvent was removed under vacuum to give a uniform solid solution. The sample was stored in a clear glass vial, under ordinary laboratory lighting, at ambient temperature and atmosphere. The stability of the formulation was followed over a period of seven days. The measurements were carried out by monitoring the absorbance of the polymer at the 250 nm peak in the electronic spectrum. No changes in the absorbance were observed in this time period.

In a second method, 2.5 g of polyethylene glycol-1450 was heated to 46° C. until completely melted. To the liquid polyethylene glycol was added 36 mg (0.232 mmol) of DEA/NO and the container was placed on a vortex mixer. A homogeneous solution was attained that gradually solidified upon cooling to ambient temperature. The stability of the solution was monitored as described above. No change in the absorbance for the 250 nm chromophore was observed at seven weeks of storage.

EXAMPLE 5

This example illustrates the preparation of a polymer composed of a polyamine/nitric oxide complex, N-[4-[1-(3-aminopropyl)-2-hydroxy-2-nitrosohydrazino)butyl]-1,3-propanediamine, zwitterionic form (SPER/NO); and polyethylene glycol (PEG) formed by the coprecipitation of the polymer and nitric oxide/nucleophilic agent.

A 1.2% (w/w) solution of KOH in polyethylene glycol-1450 (Union Carbide) was prepared in aqueous medium, and evaporated to dryness under vacuum (PEG-KOH). To 1.144 g of molten PEG-KOH was added 11.65 mg (0.042 mmol) of SPER/NO and the resulting mixture was blended to a uniform mass. No decrease was observed in the absorbance after five weeks of storage at room temperature in a clear glass vial.

EXAMPLE 6

This example describes the use of DEA/NO and SPER/NO to induce an erection in the anesthetized cat. The anesthetized cat is a well-established model of erectile response for humans. Unlike other animal models that have been employed, the cat displays both structural and pharmacological similarities to erectile response in men. For example, with the exception of some primate species, the cat is the only animal model in which response to both NO donors and prostaglandins can be observed.

Anesthetized adult male cats were given intracavernosal injections of various vasoactive agents, either alone or in combination, to determine their efficacy on intracorporal pressure and penile length change (Wang et al., J. Urol. 151: 234–237 (1994)). Each administration of a test compound was followed by the administration of a control compound so that the response of the test compound could be compared to the control compound.

DEA/NO and SPER/NO were dissolved in 10 mM NaOH and papaverine (1.65 mg), phentolamine (25 μg), prostaglandin E1 (PGE1) (0.5 μg), 200 μl vehicle, and 10 mM NaOH solution served as controls. Compounds were handled identically and administered over the dosage range of 3, 10 and 30 μg/200 μl injection.

Figure 2:
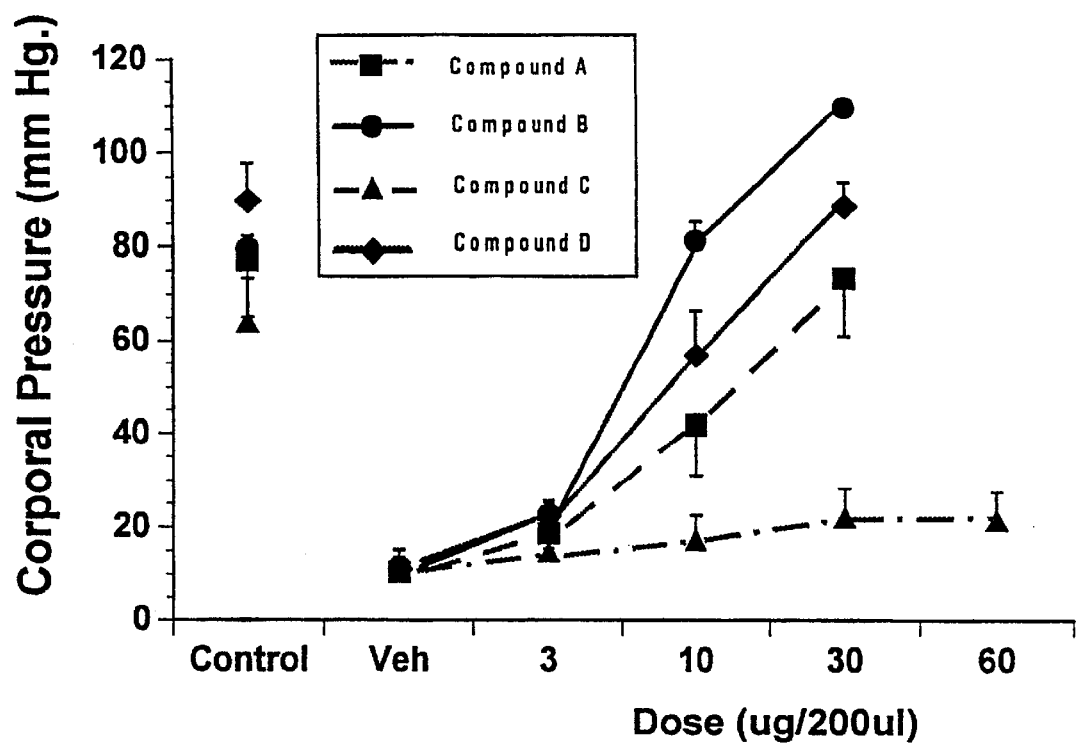
FIG. 2 is a graph of corporal pressure (mm Hg) versus dose ($\mu g/200\ \mu l$).
Figure 3:
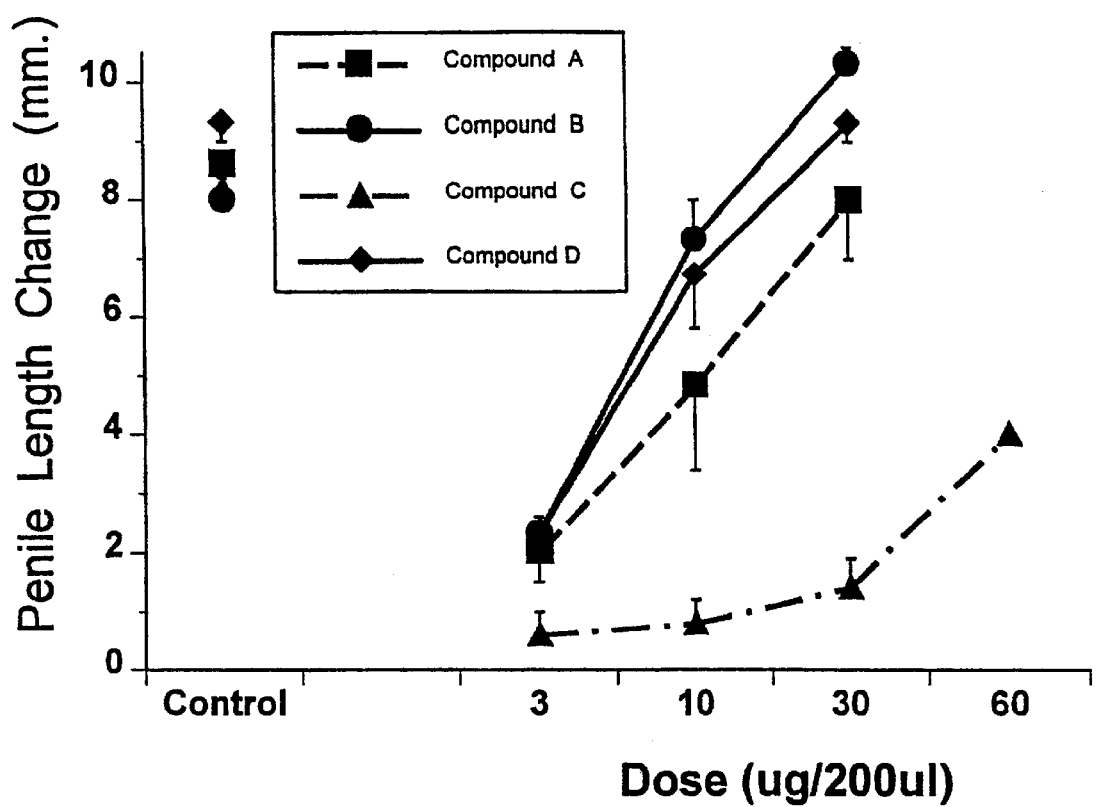
FIG. 3 is a graph of penile length change versus dose ($\mu g/200\ \mu l$).

The results of the testing are shown in FIGS. 2 and 3. FIG. 2 is a graph of corporal pressure (mm Hg) versus dose (μg/200 μl) and depicts copropral pressure response to intracavernosal injection of NONOates in anesthetized cats. The results are expressed as mean±SEM of the intracavernosal pressure response in each animal. The control is papaverine, 1.65 mg; phentolamine, 25 μg; and prostaglandin E1, 0.5 µg, in a 200 µl injection volume. Compound A is DEA/NO, compound B is prostaglandin E1 (PGE1), compound C is SPER/NO, and compound D is SNP. FIG. 3 is a graph of penile length change versus dose (µg/200 µl) and depicts penile length change in response to intracavernosal injection of NONOates in anesthetized cats. Results are expressed as mean±SEM of the change in penile length from the length recorded after vehicle administration in each animal. The control is papaverine, 1.65 mg; phentolamine, 25 µg; and prostaglandin E1, 0.5 µg, in a 200 µl injection volume. Compound A is DEA/NO, compound B is prostaglandin E1 (PGE1), compound C is SPER/NO, and compound D is SNP. The results show that increases in corporal pressure were obtained with DEA/NO (compound A), SNP (compound D) and PGE1 (compound B). An increase in penile length was obtained with SPER/NO (compound C) at a higher dose. The effect of SPER/NO appears to be related to its relative potency as well as its longer rate of release of NO.

The results show the usefulness of NONOates as NO donors for the treatment of erectile dysfunction. DEA/NO produced erections of comparable pressure, size and duration to that produced by combined treatment with papaverine, phentolamine and PGE1, which has been successfully used to treat men with organic dysfunction. The results suggest that DEA/NO and SPER/NO can be used together in a synergistic manner to produce erections of rapid onset and sufficient rigidity and duration.

All publications, patents, and patent applications cited herein are hereby incorporated by reference to the same extent as if each individual document were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A method for the treatment of impotency in a male animal, which method comprises the administration to said male animal of a nitric oxide-releasing agent, wherein said agent is a polyether capable of releasing nitric oxide, wherein said polyether comprises at least one nitric oxide-releasing [$N_2O_2$] functional group selected from the group consisting of X—[N(O)NO] and [N(O)NO]—X, wherein X is a moiety bonded to said —[N(O)NO] or [N(O)NO]—, and wherein said —[N(O)NO] or [N(O)NO]— group is bound covalently to an oxygen or carbon atom of said polyether through said moiety X, said agent providing a penile erection-inducing amount of nitric oxide to said male animal.

2. The method of claim 1, wherein said nitric oxide-releasing [$N_2O_2$] functional group is from a compound of the formula selected from the group consisting of I, II, III, IV, V, VI, VII and VIII as follows:

(I)
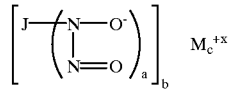

wherein J is an organic or inorganic moiety, $M^{+x}$ is a pharmaceutically acceptable cation, where x is the valence of the cation, a is 1 or 2, and b and c are the smallest integers that result in a neutral compound;

(II)
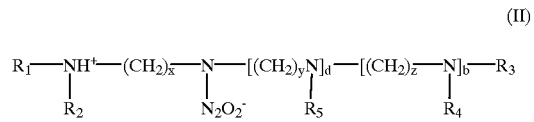

wherein b and d are the same or different and are zero or one, $R_1$, $R_2$, $R_3$, $R_4$, and $R_5$ are the same or different and are hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12;

(III)

wherein B is

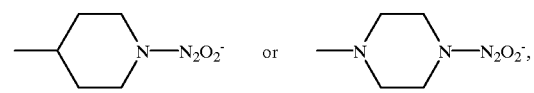

$R_6$ and $R_7$ are the same or different and are hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, f is an integer from 0 to 12, with the proviso that when B is the substituted piperazine moiety

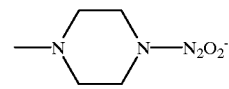

then f is an integer from 2 to 12;

(IV)
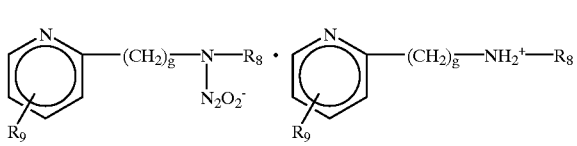

wherein $R_8$ is hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, $R_9$ is hydrogen or a $C_{1-12}$ straight or branched chain alkyl, and g is 2 to 6;

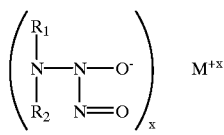  (V)

wherein $R_1$ and $R_2$ are independently selected from the group consisting of a $C_1$–$C_{12}$ straight or branched chain alkyl and benzyl, $M^{+x}$ is a pharmaceutically acceptable cation, and x is the valence of the cation;

$$K[(M)^{x'}_x(L)_y(R^1R^2N{-\!\!\!-}N_2O_2)_z]$$  (VI)

wherein M is a pharmaceutically acceptable metal, or where x is at least two, a mixture of two different pharmaceutically acceptable metals, L is a ligand different from ($R^1R^2N$—$N_2O_2$) and is bound to at least one metal, $R^1$ and $R^2$ are each organic moieties and are the same or different, x is an integer of from 1 to 10, x' is the formal oxidation state of the metal M, and is an integer of from 1 to 6, y is an integer of from 1 to 18, with the proviso that y is at least 2, the ligands L are the same or different, z is an integer from 1 to 20, and K is a pharmaceutically acceptable counterion to render the compound neutral to the extent necessary;

$$[R{-\!\!\!-}N(H)N(NO)O{-\!\!\!-}]_y X$$  (VII)

wherein R is $C_{2-8}$ lower alkyl, phenyl, benzyl, or $C_{3-8}$ cycloalkyl, any of which R groups can be substituted by one to three substituents, which are the same or different, and are selected from the group consisting of halo, hydroxy, $C_{1-8}$ alkoxy, —$NH_2$, —C(O)$NH_2$, —CH(O), —C(O)OH, and —$NO_2$, X is a pharmaceutically acceptable cation, a pharmaceutically acceptable metal center, or a pharmaceutically acceptable organic group selected from the group consisting of $C_{1-8}$ lower alkyl, —C(O)$CH_3$, and —C(O)$NH_2$, and y is an integer from 1 to 3, consistent with the valence of X; and

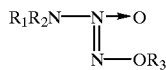  (VIII)

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, a $C_{3-12}$ straight or branched chain olefinic unsubstituted or substituted with hydroxy, alkoxy, acyloxy, halo or benzyl, or $R_1$ and $R_2$ together with the nitrogen atom to which they are bonded form a heterocyclic group, and $R_3$ is a group selected from $C_{1-12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_{1-12}$ unsubstituted or substituted acyl, sulfonyl and carboxamido; or $R_3$ is a group of the formula —$(CH_2)_n$—ON=N(O)$NR_1R_2$, wherein n is an integer of 2–8, and $R_1$ and $R_2$ are as defined above.

3. The method of claim 2, wherein said nitric oxide-releasing [$N_2O_2$] functional group is from a compound of formula III, and B is the substituted piperazine moiety

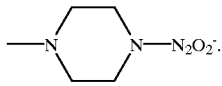

4. The method of claim 2, wherein said nitric oxide-releasing [$N_2O_2$] functional group is from a compound of formula V, and $R_1$ and $R_2$ are selected so that $R_1$ and $R_2$, together with the nitrogen atom to which they are bonded, form a heterocyclic group.

5. The method of claim 4, wherein the heterocyclic group is selected from the group consisting of pyrrolidino, piperidino, piperazino and morpholino.

6. The method of claim 2, wherein said nitric oxide-releasing [$N_2O_2$] functional group is from a compound of formula VIII, and the heterocyclic group is selected from the group consisting of pyrrolidino, piperidino, piperazino, and morpholino.

7. The method of claim 1, wherein the moiety X of said functional group is part of the polymeric backbone.

8. The method of claim 1, wherein the moiety X of said functional group is part of a group pendant to the polymeric backbone.

9. A method for the treatment of impotency in a male animal, which method comprises administering to said male animal a nitric oxide-releasing agent, said agent being a nitric oxide delivery means comprising a polyether, wherein said polyether comprises at least one nitric oxide-releasing [$N_2O_2$] functional group selected from the group consisting of X—[N(O)NO] and [N(O)NO]—X, wherein X is a moiety bonded to said —[N(O)NO] or [N(O)NO]—, and wherein said —[N(O)NO] or [N(O)NO]—group is bound covalently to an oxygen or carbon atom of said polyether through said moiety X, said agent providing a penile erection-inducing amount of nitric oxide to said male animal.

10. The method according to claim 9, wherein said nitric oxide delivery means is a transurethral applicator.

* * * * *